United States Patent
Zientara-Rytter et al.

(10) Patent No.: US 9,534,229 B2
(45) Date of Patent: Jan. 3, 2017

(54) PLANT HOMOLOG TO AUTOPHAGY PROTEIN P62

(75) Inventors: Katarzyna Zientara-Rytter, Wiązowna (PL); Grzegorz Moniuszko, Białystok (PL); Anna Wawrzyńska, Pruszków (PL); Jolanta Łukomska, Rypin (PL); Agieszka Sirko, Warsaw (PL)

(73) Assignee: INSTYTUT BIOCHEMII I BIOFIZYKI PAN, Warsaw (PL)

( * ) Notice: Subject to any disclaimer, the term of this patent is extended or adjusted under 35 U.S.C. 154(b) by 514 days.

(21) Appl. No.: 13/881,670

(22) PCT Filed: Oct. 27, 2011

(86) PCT No.: PCT/PL2011/000111
§ 371 (c)(1),
(2), (4) Date: Dec. 2, 2013

(87) PCT Pub. No.: WO2012/057640
PCT Pub. Date: May 3, 2012

(65) Prior Publication Data
US 2014/0259214 A1    Sep. 11, 2014

(30) Foreign Application Priority Data
Oct. 27, 2010  (PL) ........................................ 392772

(51) Int. Cl.
C12N 15/82    (2006.01)
A01H 5/00     (2006.01)
C07K 14/415   (2006.01)

(52) U.S. Cl.
CPC ......... *C12N 15/8271* (2013.01); *C07K 14/415* (2013.01); *C12N 15/8261* (2013.01)

(58) Field of Classification Search
None
See application file for complete search history.

(56) References Cited

U.S. PATENT DOCUMENTS

2006/0090219 A1    4/2006    Kisaka et al.

FOREIGN PATENT DOCUMENTS

| CA | 2701871 A1 | 3/2009 |
|----|------------|--------|
| WO | 0233051 A1 | 4/2002 |
| WO | 2007126850 A2 | 11/2007 |
| WO | 2010071995 A1 | 7/2010 |

OTHER PUBLICATIONS

Kraft et al., 2010, Nature Cell Biology 12: 836-841.*
Yoshimoto et al., 2010, FEBS Letters 584: 1350-1358.*
Contento et al., 2005, The Plant Journal 42: 598-608.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Svenning, 2006, MSc Thesis, University of Tromsø, pp. 1-108.*
Matsuoka and Klionsky, 2008, In: Methods in Enzymology, Academic Press, pp. 541-555.*
GenBank Accession No. DQ444220 (ver. DQ444220.1), published Jul. 1, 2006.*
Paterson, Andrew H., et al., "The Sorghum Bicolor Genome and the Diversification of Grasses," Nature, Jan. 29, 2009, 551-556, vol. 457, Macmillan Publishers Limited, London.
Larsen, Kenneth Bowitz, et al., "A Reporter Cell System to Monitor Autophagy based on p62/SQSTM1," Autophagy, Aug. 16, 2010, 784-793, vol. 6, Issue 6, Landes Bioscience, USA.
Lamark, Trond, et al., "NBR1 and p62 as Cargo Receptors for Selective Autophagy of Ubiquitinated Targets," Cell Cycle, Jul. 1, 2009, 1986-1990, vol. 8, Issue 13, Landes Bioscience, USA.
Yoshimoto, Kohki, et al., "Autophagy in Plants and Phytopathogens," FEBS Letters, Jan. 14, 2010, 1350-1358, vol. 584, Issue 7, Elsevier, Amsterdam.
Zientara-Rytter, Katarzyna, et al., "Identification and Functional Analysis of Joka2, a Tobacco Member of the Family of Selective Autophagy Cargo Receptors," Autophagy, Oct. 1, 2011, 1145-1158, vol. 7, Issue 10, Landes Bioscience, USA.
Bei, C.L., et al., "DQ211935.1 Triticum Aestivum Ubiquitin-Associated Protein (UBA) mRNA, Complete Cds.," NCBI, Dec. 31, 2008.

* cited by examiner

*Primary Examiner* — Amjad Abraham
*Assistant Examiner* — Bratislav Stankovic
(74) *Attorney, Agent, or Firm* — Walker & Jocke

(57) ABSTRACT

The present invention comprises recombinant DNA molecule, expression cassette, DNA vector, binary plasmid, plant cell and a method of polypeptide production in eukaryotic organism and use thereof. In more details, it provides the means, through using methods of genetic engineering, of obtaining plants with advantageous breeding features, particularly with increased tolerance to abiotic stresses including mineral deficiency or plants useful for monitoring the process of autophagy.

7 Claims, 2 Drawing Sheets

PLANT HOMOLOG TO AUTOPHAGY PROTEIN P62

The present invention comprises recombinant DNA molecule, expression cassette, DNA vector, binary plasmid, plant cell and a method of polypeptide production in eukaryotic organism and use thereof. In more details, it provides the means, through using methods of genetic engineering, of obtaining plants with advantageous breeding features, particularly with increased tolerance to abiotic stresses including mineral deficiency or plants useful for monitoring the process of autophagy.

The transgenic crop plants, obtained according to the present invention overproduce Joka2 protein, a member of the Joka2/p62/NBR1 family in fusion with a fluorescent protein. The plants overproducing Joka2 with or without fusion with a fluorescent protein are applicable, for example, in agriculture because of their higher tolerance to environmental stresses and better green biomass production in suboptimal conditions of growth.

Autophagy is a ubiquitous catabolic process in eukaryotic cells. Although it was first described about 40 years ago, molecular understanding of this process started only about a decade ago (Klionsky, 2007; Klionsky et al., 2010). There are several types of autophagy, of which the best characterized is macroautophagy. During this process structures called autophagosomes, surrounded by double-membranes are created. The cargos such as, cell organelles, soluble proteins and protein aggregates are sequestered for degradation into the autophagosomes. In the subsequent steps of autophagy, the autophagosome is taken (soaked) into the vacuole where it stays enclosed only by the inner autophagosomal membrane, while the outer membrane of the autophagosome fuses with the vacuole membrane. Then, the cargo is degraded and the products of degradation are released for reuse within other metabolic pathways. At least 34 various proteins, which transiently associate and act in a hierarchical order during autophagosome formation, were described so far. Genes encoding these proteins were initially found and characterized in yeasts (Nakatogawa et al., 2009), however it is now clear that the entire process, as well as its individual elements are evolutionarily conserved (Yang and Klionsky, 2010). On the other hand, it seems that in higher eukaryotes the process of autophagy require additional, more elaborate molecular elements, which are absent in yeast cells.

Recently, it has been shown that the autophagy has a tremendous influence on protein homeostasis in humans (Behrends et al., 2010). It is needed for appropriate response to nutrient stress, innate and adaptive immunity and autophagic programmed cell death. Malfunction of autophagy has been linked to a wide range of human pathologies, including cancer, different neurodegenerative diseases, immunological disorders and pathogen infection (Jo, 2010; Moreau et al., 2010: Walsh and Edinger, 2010). Autophagy is also important during development processes of mammals, flies and worms (Melendez and Neufeld, 2008).

Autophagy has been intensively examined in humans but it has only been recently established in plants. Studies on autophagy in plants are greatly facilitated by the functional and structural conservation of the ATG proteins participating in autophagy and of the process itself (Reumann et al., 2010; Diaz-Troya et al., 2008; Yoshimoto et al., 2010). Analyses of many available atg mutants (in genes related to autophagy) revealed that autophagy is an essential process also in plants, as many of these mutants senescent earlier and are hypersensitive to nitrogen starvation and carbon limitation (Doelling et al., 2002; Phillips et al., 2008; Thompson et al., 2005; Thompson and Vierstra, 2005; Yoshimoto et al., 2004).

Autophagy process could be induced in plants after their treatment by reagents evoking oxidative stress (Xiong et al., 2007). It has been also shown that under the conditions of nitrogen limitation the process of autophagy is involved in degradation of RUBISCO and whole chloroplasts (Ishida et al., 2008; Wada et al., 2009). In general, it is consider that autophagy acts as a molecular cell survival mechanism that in the conditions of nutrient deprivation provides survival through recycling nutrients and other cellular components. However, autophagy in plants is essential also during such biological stresses as pathogen infections (Liu et al., 2005; Patel and Dinesh-Kumar, 2008); (Yoshimoto et al., 2009) and in conditions of normal growth (Inoue et al., 2006; Moriyasu et al., 2003).

In addition to the proteins participating in the core autophagy process there also exist cargo receptors of selective autophagy. These proteins recognize specific cargos and sequester them for degradation (Kirkin et al., 2009a; Kirkin et al., 2009b; Komatsu et al., 2007; Pankiv et al., 2007). In mammalian cells at least two proteins (p62/SQSTM1/Sequestosome-1 and NBR1 (neighbor of BRCA1 gene 1)) can bind protein aggregates designated for degradation and deliver them to the autophagosomes. Most published data describe the function of p62, which itself is degraded by autophagy (Komatsu and Ichimura, 2010; Komatsu et al., 2010). It has been shown that the p62 facilitates the clearance of the ubiquitinated proteins aggregates trough the process of autophagy. The protein aggregates accumulating in various chronic, toxic and degenerative diseases have been linked to the defects in autophagy process (Du et al., 2009a; Du et al., 2009b; Komatsu et al., 2010; Mathew et al., 2009).

Until recently, it has been believed that no selective autophagy receptors exist in plants (Yoshimoto et al., 2010). Surprisingly, it has been shown by our group that the Joka2 protein is actually a structural and a functional homolog of the cargo receptors of selective autophagy. The Joka2 protein has similar domain architecture as mammalian p62 and NBR1 proteins. Moreover, plants with constitutive ectopic expression of Joka2::YFP or Joka2::CFP are more tolerant to nutrient deficiency manifested by lesser yellowing of the leaves in the conditions of nutrient starvation. The fusions of Joka2 with fluorescent proteins may be used as a molecular marker of autophagosomes and as an indicator (or reporter) for monitoring the process of selective autophagy in plants. Similar applications of p62 protein in reference to mammal cells were previously described (Larsen et al., 2010). The Joka2 protein has not been used before in plant cells as an autophagy marker because of the lack of the proof that Joka2 is an orthologue of mammalian receptors of selective autophagy, such as p62 or NBR1.

Several patents consider possibility of improving crop yield by introducing into the crop genomes the specific genes by the genetic engineering methods, some of them include autophagy related genes. In the patent application WO0233051 (published 2002 Apr. 25) recombinant plant proteins that function as regulators of autophagy, such as AUT1 proteins are described, as are nucleotide sequences encoding these proteins. Further described are recombinant vectors, host cells, transgenic plants, and methods for using the nucleic acid molecules and proteins of the invention. According to the current nomenclature the AUT1 corresponds to ATG3. A method for improving the yield of a plant is presented in the patent application WO2007126850 (published 2007 Nov. 8). The method uses genetic engineering techniques for transformation of plants to introduce expression cassettes for over- or under-expression of genes involved in photoperiodic control of floret differentiation and degradation. Such methods provide for increased yield at harvest when compared to wild-type plants, however the genes are not related to autophagy. Plants with increased yield are described also in the patent application CA2701871 (published 2009 Mar. 26). This invention relates generally to a plant cell with enhanced nitrogen use efficiency and/or increased biomass production as compared to a corresponding non-transformed wild type plant cell by increasing or generating one or more activities of polypeptides associated with enhanced nitrogen use efficiency in plants. In the patent application WO2010071995 (published 2010 Jul. 1) TOR-interacting proteins (TIPS) and genes encoding them are described. Broad experimental tools that include biochemical molecular developmental global genomics and loss and gain of function transgenic approaches have been applied to address target of rapamycin (TOR) signaling pathway in plants especially using *Arabidopsis* model system and *Brassica napus* crop. Towards this objective, putative TOR interacting proteins (TIPs) have been identified and functions of these implicated in diverse developmental and biochemical processes have been investigated. Functional studies including overexpression and silencing of TIPs have shown a range of phenotypes that include nutrition-use-efficiency, altered plant architecture and stress resistance in transgenic *Arabidopsis* and *Brassica* lines. Some of these phenotypes are relevant to important developmental pathways implicated in canola crop yield and performance. Autophagy is induced through the TOR signaling pathway.

The invention described in patent application US20060090219 (published 2006 Apr. 27) provides a method of producing a plant which exhibits improved growth and/or yield under reduced nitrogen conditions, that is, under cultivation conditions where nitrogen is limited as compared to ordinary cultivation conditions, by increasing 2-OG content in plants. Introducing a GDH gene or ECASPC gene into plants and expressing the transgene GDH or ECAPS in the plants results in increased 2-OG, or by spraying proline on the leaves of plants to increase the 2-OG content, thereby enhancing the incorporation of nitrogen or metabolic activity of plants. The invention also provided is a method of cultivating such plants under nitrogen-limited conditions.

Brief Description

Figure 1:
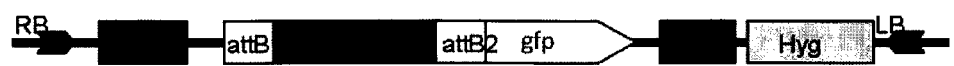
FIG. 1 schematically shows details of the constructed expression cassettes, where gfp stands for yfp in the case of pJ4 and for cfp in the case of pJ5, attB1 and attB2 are the recombination sites related to the cloning method (Gateway® system); P35S and T35S are promoter and terminator of the 35S gene of cauliflower mosaic virus, respectively; HYG is the selection marker; LB and RB are the left and right borders of the T-DNA inserted into the plant genome, respectively.

Despite of high existing state of technology there is still need of increasing plant tolerance to biotic and abiotic stresses and obtaining crops with higher yield. Abiotic stresses, such as mineral deficiency, decrease chlorophyll content and photosynthesis process in plants what, in turn, increases leaf chlorosis and senescence. Autophagy plays a major role in plant survival during starvation conditions due to recycling of the cellular components and improving their reuse. In addition, it seems that autophagy is a fundamental biological process that plays a crucial role in normal growth and development. Interestingly, Joka2 combines unique features of two typical mammalian cargo receptors for selective autophagy, NBR1 and p62. Moreover, importance of Joka2 in plant nutrition was confirmed by some phenotypes observed in tobacco plant with constitutive ectopic expression of Joka2::YFP or Joka2::CFP, which in the conditions of nutrient deficiency had less yellow leaves than parental plants.

In this invention transgenic plants containing expression cassette, stably integrated into genome and enabling production of the "chimeric" Joka2::YFP or Joka2::CFP proteins, have been described. The Joka2 protein belongs to the family of selective autophagy cargo receptors. The plants have been created by the genetic engineering methods. The approach and the proteins described in the present invention can be used for increasing crop tolerance to abiotic stresses and for achieving more efficient biomass production, especially in the conditions of limiting nutrients availabilities. Additionally, monitoring of the location and the amounts of the "chimeric" proteins enables monitoring of the autophagy process in plants.

The present invention comprises a recombined DNA molecule comprising of the sequence according to SEQ. ID No. 1 and encoding protein from the family of Joka2/p62 or its characteristic domains.

According to present invention, the recombinant DNA molecule contains the nucleotide sequence preferably encoding polypeptide or protein, which is in at least 30% similar to the protein encoded by sequence shown in SEQ. ID No. 1 and comprises the protein domains typical to the family Joka2/p62.

Preferably, according to present invention, the recombinant DNA molecule contains nucleotide sequence encoding a protein factor from the Joka2/p62 family, preferably selected from the group of the proteins able to increase plant tolerance to the abiotic stresses and/or improving nutrient use efficiency in comparison to the parental plants.

Preferably, according to present invention, the recombinant DNA molecule is functionally linked to a nucleotide sequence encoding the marker protein, preferably selected from the group of fluorescent proteins.

Preferably, according to present invention, the said DNA molecule contains sequence encoding additional protein marker functionally linked with the protein from the Joka2/p62 family, enabling in situ monitoring of production and localization of the said protein.

Preferably, according to present invention, the fluorescent proteins comprise YFP or CFP.

The expression cassette, containing recombinant DNA molecule described above, is functionally linked to regulatory elements allowing either stable or transient expression of the said DNA molecule in a plant cell.

The plasmid or viral vectors used for plant-based expression contain the said expression cassette with at least one recombinant DNA molecule described above.

The binary plasmid containing the said expression cassette with at least one recombinant DNA molecule described above and containing the selection marker enabling positive selection of the plant cells containing recombinant DNA molecule incorporated into genome.

The plant cell containing recombinant DNA molecule described above.

A method of producing protein in eukaryotic host by incorporating into the host genome the recombinant DNA molecule described above.

Preferably, the DNA molecule encoding protein from the Joka2/p62 family is first cloned into the vector containing the regulatory elements enabling expression in plant cells, next the plant expression cassette is transferred into the binary vector and next, the expression cassette is transferred along with the selection markers into the plant genome, next the transgenic plants capable of production of the protein from the Joka2/p62 family in fusion with the fluorescent protein are regenerated and selected.

Preferably, the binary plasmid enables a positive selection of plant cells containing recombinant DNA molecule incorporated into the genome.

Preferably, if plasmid contains the additional marker functionally linked as a translational fusion with the protein from the Joka2/p62 family, wherein the said marker enables in situ monitoring of the said protein production and localization.

Preferably, the recombinant DNA molecule is introduced into the plant cell using any known method of introducing the genetic material into the plant cells depending on the plant host, wherein the stable integration into the host genome is achieved.

Preferably, the recombinant DNA molecule is introduced into the plant cell using any known method of introducing the genetic material into the plant cells depending on the plant host, wherein the transient expression of the expression cassette described above is achieved.

Preferably, the obtained transgenic plants have increased nutrients use efficiency, better growth and increased tolerance to nutrients deficit and other abiotic stress in comparison to the parental lines, which do not contain the DNA molecule described above.

Use of recombinant DNA molecule according to the present invention for production of a protein from the family of Joka2/p62 in plant cells.

Preferably, the obtained plants produce protein from the Joka2/p62 family as a fusion or fusionless protein and have increased nutrients use efficiency, better growth and increased tolerance to nutrients deficit and other abiotic stress in comparison to the parental lines, which do not contain the DNA molecule described above.

Preferably, the obtained plants produce the fusion or fusionless protein from the Joka2/p62 family, which can be used for monitoring of autophagy and labeling the autophagosomes.

A method, according to present invention, of introducing to the host genome the genetic material comprising of the expression cassette described above containing the joka2 gene from *Nicotiana tabacum*, obtained from the plant material by the known methods.

A plasmid used for genetic transformation contains the sequence encoding Joka2 protein, 35S promoter from cauliflower mosaic virus (CaMV) known to initiate transcription in plant cells and transcriptional terminator known to terminate transcription in plant cells downstream the sequence encoding either Joka2 or Joka2 functionally linked to fluorescent protein.

Proteins from the Joka2/p62 family are weakly conserved if complete protein sequences are compared. The percentage of identical amino acids between the Joka2 from *Nicotiana tabacum* and its homologues from other organisms is as following: 34.9% *Zea mays*, 35.1% *Triticum aestivum*, 37.9% *Oryza sativa*, 42% *Vitis vinifera*, 45% *Populus trichocarpa*, 49.4% *Arabidopsis thaliana*, 30.3% *Homo sapiens*. It is difficult to classify the protein as the member of the family based only on the total number of identical amino acids, however in these proteins all characteristic domains essential for their function in selective autophagy are conserved.

A method according to present invention is used for: (1) Isolation and amplification of the DNA molecule encoding joka2 and cloning it into the intermediate vector, (2) Transfer of the joka2 sequence to the plasmid enabling formation of the plant expression cassette, such as transcriptional promoter, terminator and the sequence encoding fluorescent protein, (3) Transfer of the expression cassette to the binary plasmid enabling plant transformation, (4) Transfer of the plant expression cassette to the plant cell, (5) Regeneration and selection of transgenic plants able to produce Joka2 protein with or without fusion with the fluorescent proteins.

Plants obtained according to present invention are overproducing Joka2 protein with or without fusion with fluorescent proteins and because of the increased content of the protein from the Joka2/p62 family they are more tolerant to the abiotic stress and have increased nutrient use efficiency.

The genetic material used in the method according to present invention, preferably comprises of binary plasmid, preferably containing selection marker enabling positive selection of plant cells containing the expression cassette. In addition, such plasmid preferably contains marker functionally linked with the protein from the Joka2/p62 family enabling in situ monitoring of production and localization of the said protein.

The plant expression cassette can be introduced into the plant cell using any known method. The choice of the method depends on the host plant and it should enable stable incorporation of the cassette into the plant genome, what in turn enables its inheritance and stability in the next generations. The examples include usage of *Agrobacterium*-mediated transformation.

A method according to present invention can be used for obtaining plants with better growth and increased tolerance to nutrients deficiency and possibly other abiotic stresses in comparison to the parental plants.

It is probable that the plants obtained according to present invention will have increased nutrient use efficiency due to the process of recycling of nutrients in the process of selective autophagy. The process is facilitated in plants containing higher amount of the protein from the Joka2/p62 family.

EXAMPLES

Example 1

Construction of Expression Cassettes Containing a Recombinant DNA Molecule with Joka2 cDNA from *Nicotiana tabacum* in Fusion with a cDNA Encoding Fluorescent Protein A plasmid was developed for plant-based expression of a translational fusion of the Joka2 cDNA from *Nicotiana tabacum* and the cDNA encoding either YFP or CFP protein. To obtain the complete Joka2 cDNA, total RNA was isolated from tobacco plants grown for 2-days without sulfur source. The phenol-chloroform method described previously by Linthorst (Linthorst et al., 1993) was used for extraction. The total RNA isolated from the plants grown in the said conditions was used for cDNA library construction by reverse transcriptase (RT) reaction and, subsequently, polymerase chain reaction (PCR). The RT-PCR reaction was performed using commercially available "SuperScriptII Reverse Transcriptase" kit and oligo (dT) primer from Invitrogen. The obtained cDNA library served as a template and the following pair of nucleotides: 5'-ggggacaagtttgta-caaaaaagcaggctcaatggctatggagtctgctat-3' (Seq. ID No. 2) and 5'-ggggaccactttgtacaagaaag ctgggtcctgctctccag-caataagatc-3' (Seq. ID No. 3) served as primers in the reaction used to amplify Joka2 by recombinant Taq polymerase from Fermentas. First, the 2.2-kb PCR product was cloned into the entry vector pDEST221 (Invitrogen). The subsequent cloning was performed using the Gateway system. The pDEST221 vector with correct Joka2 sequence (Seq. ID No. 1) was used in two reactions of homologous recombination, which resulted in inserting of the DNA molecule described previously into two plant binary vectors, pH7YWG2 and pK7CWG2 (Karimi et al., 2002). The obtained binary plasmids containing translational fusions joka2::yfp and joka2::cfp were named pJ4 and pJ5, respectively. The pJ4 and pJ5 binary plasmids were introduced separately by electroporation into the LBA4404 strain of *Agrobacterium tumefaciens*. The details of the constructed expression cassettes are schematically shown in FIG. 1, where gfp stands for yfp in the case of pJ4 and for cfp in the case of pJ5; attB1 and attB2 are the recombination sites related to the cloning method (Gateway system); P35S and T35S are promoter and terminator of the 35S gene of cauliflower mosaic virus, respectively; HYG is the selection marker; LB and RB are the left and right borders of the T-DNA inserted into the plant genome, respectively.

Example 2

*Agrobacterium*-Mediated Transformation of Tobacco Plants with the Binary Plasmid Containing Expression Cassettes Containing a Recombinant DNA Molecule Tobacco (*Nicotiana tabacum*) was chosen, as a model plant for stable plant transformation due to the simplicity of its transformation and analysis methods. The low alkaloids line of tobacco, LA Burley 21 (Legg et al., 1970), was used for transformation.

Seeds, after surface sterilization by bleach, were germinated in vitro on Murashige and Skoog medium (Murashige and Skoog, 1962). The 2-3-weeks old tobacco seedlings were transformed using the suspensions of the *Agrobacterium tumefaciens* cells harboring the described above plasmids, pJ4 or pJ5.

The regenerated tobacco plants growing on selective medium containing kanamycin or hygromycin as a selection markers were verified by immunodetection of Joka2::CFP or Joka2::YFP in the plant material. Several transgenic lines with the highest expression of the transgenes, as detected by western-blots, were selected and transferred to the green house. The next generations of transformants were obtained by self-pollination. Plants from the next generation (T1) were additionally analyzed by western-blot and by confocal fluorescent microscopy.

Example 3

Analysis of Subcellular Localization of the Fusion Protein JOKA2::YFP in the Transgenic Tobacco Lines Containing Recombinant DNA Molecule The transgenic lines J4-1 J4-2, J4-10, J5-1, J5-2, J5-3 and J5-6 were chosen for further analysis. Seeds of the transgenic J4- and J5-lines and of the control plants, including parental line (LAB21) and line AB5 (overproducing EGFP protein) were germinated either in distilled water, or in two kinds of modified 0.5× Hoagland media, either complete (nS) or lacking sulfur (S—), where the equimolar amounts of $MgCl_2$ replaced $MgSO_4$.

Figure 2:
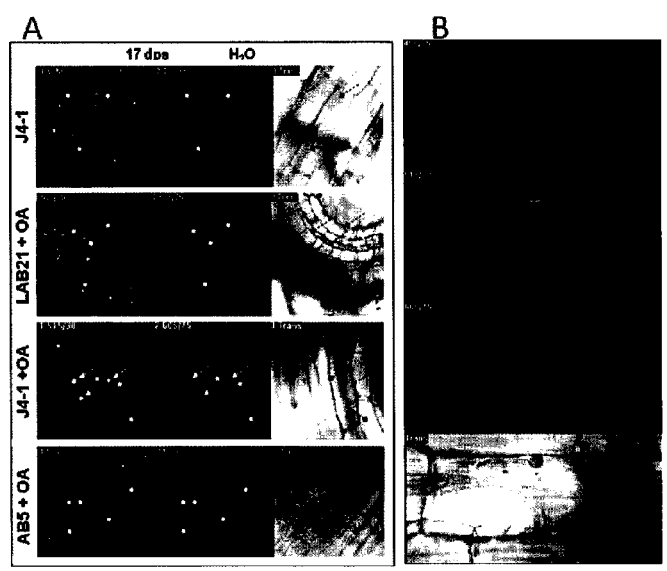
FIG. 2A shows observed fluorescent signal in small acidic cytosolic granules similar to autophagosomes
FIG. 2B shows observed fluorescent signal observed in the nucleus.

The seedlings were incubated in a growth chamber under a long-day regime of 16 h light/8 h dark cycle at 24° C. After 10, 17 and 33 days of the treatment, seedlings were taken for observation under a confocal microscope Eclipse TE2000-E from Nicon. Analysis showed that fusion proteins Joka2::YFP and Joka2::CFP are localized in two different cellular compartments. Fluorescent signal was observed in nucleus (FIG. 2B) and in small acidic cytosolic granules similar to autophagosomes (FIG. 2A). Dual cellular localization of Joka2::YFP protein was confirmed by observation of co-localization of fluorescent signal from the fusion protein and the respective fluorescent dyes. For nuclei visualization (FIG. 2A, blue color), the single DAPI-staining was used where DAPI dye was solved in DMSO to final concentration 0.1 µg/ml. For acid compartments (such as autophagosomes, FIG. 2A) visualization, the Acridine Orange (AO) resolved in water to final concentration 1 µg/ml was used. The AO dye has been previously used to stain the autophagosomes in mammals. Tobacco seedlings were incubated with DAPI or AO for 15 minutes in the darkness at room temperature for staining After the treatment, seedlings were washed in water to decrease fluorescent background. Acidic granules were visible after AO staining only in plants overexpressing fusion protein but not in the control plants.

Figure 3:
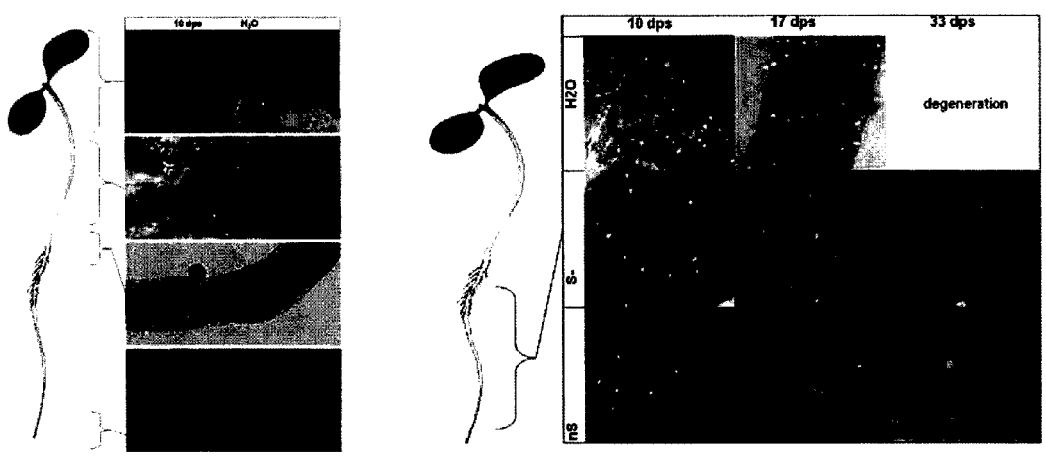
FIG. 3 shows localization of Joka2::YFP in J4-1.

Since no apparent differences between J4 and J5 lines were noticed, localization of Joka2::YFP in J4-1 seedlings is shown as a typical example (FIG. 3). Cellular localization of fluorescent protein in green parts and in the root tip was stable and not affected by the differences in the conditions of growth and age of seedlings (FIG. 3, the left-hand panel). However, distribution of Joka2::YFP or Joka2::CFP in the roots varied depending on the root part, the growth medium (normal medium [nS], medium without S [S—] or water [$H_2O$]) and the seedlings age (FIG. 3, the right-hand panel). Initially (10 days post sawing [10 dps]), the fluorescent signal was observed in the numerous, small cytosolic granules that were present in whole cytoplasm. Later (17 days post sawing [dps]), the granules were larger, less frequent (1-2 per cell) and located close to the nucleus. In the oldest seedlings (33 days post sawing [33 dps]), the fluorescence was observed mostly in the nucleus.

Example 4

Figure 4:
FIG. 4 shows phenotypic differences between control lines and transgenic plants producing Joka2::YFP or Joka2:: CFP have been observed when plants were grown in nutrient deficient conditions in comparison with two control lines, WT and AB5
Figure 5:
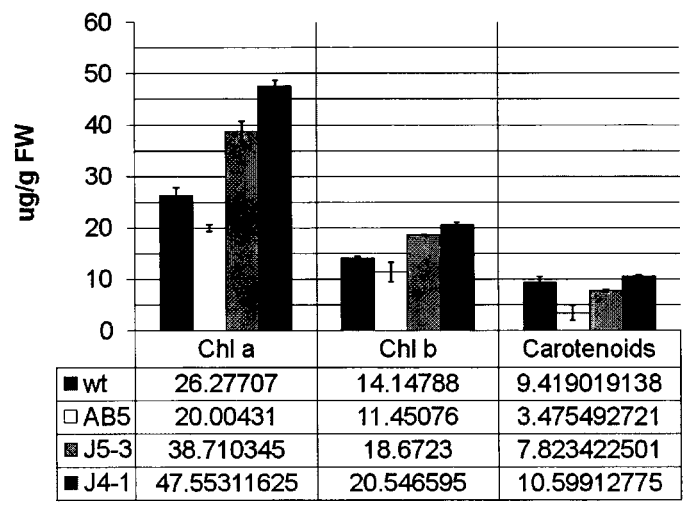
FIG. 5 shows the detection of the increased contents of chlorophylls, namely chlorophyll a (Chl a) and chlorophyll b (Chl b) in plants J4-1 and J5-3 in comparison to the control lines (WT and AB5).

Attenuated Response to Nutrient Deficiency Conditions of Transgenic Tobacco Plants Overproducing Fusion Protein Joka2::YFP Phenotypic differences between control lines and transgenic plants producing Joka2::YFP or Joka2::CFP have been observed when plants were grown in nutrient deficient conditions. Transgenic plants (J4-1 and J5-3) were greener (had lesser yellowing of the leaves) in comparison with two control lines, WT and AB5 (FIG. 4). These visible differences were biochemically confirmed by detection of the increased contents of chlorophylls, namely chlorophyll a (Chl a) and chlorophyll b (Chl b) in plants J4-1 and J5-3 in comparison to the control lines (WT and AB5) (FIG. 5). To exclude the possibility that the performance of the seedlings was linked to the mass of the seeds, the weight of 200 seeds from each line was determined in triplicates. The calculated average values (14.87±0.23 mg for the parental (WT) line, 14.13±0.66 mg for AB5 and, as an example 14.17±1.83 mg for J4-1) revealed a lack of association of the response to mineral deficiency with the seed mass.

REFERENCES

Behrends C, Sowa M E, Gygi S P, Harper J W. 2010. Network organization of the human autophagy system. *Nature* 466, 68-76.

Diaz-Troya S, Perez-Perez M E, Florencio F J, Crespo J L. 2008. The role of TOR in autophagy regulation from yeast to plants and mammals. *Autophagy* 4, 851-865.

Doelling J H, Walker J M, Friedman E M, Thompson A R, Vierstra R D. 2002. The APG8/12-activating enzyme APG7 is required for proper nutrient recycling and senescence in *Arabidopsis thaliana*. *J Biol Chem* 277, 33105-33114.

Du Y, Wooten M C, Gearing M, Wooten M W. 2009a. Age-associated oxidative damage to the p62 promoter: implications for Alzheimer disease. *Free Radic Biol Med* 46, 492-501.

Du Y, Wooten M C, Wooten M W. 2009b. Oxidative damage to the promoter region of SQSTM1/p62 is common to neurodegenerative disease. *Neurobiol Dis* 35, 302-310.

Inoue Y, Suzuki T, Hattori M, Yoshimoto K, Ohsumi Y, Moriyasu Y. 2006. AtATG genes, homologs of yeast autophagy genes, are involved in constitutive autophagy in *Arabidopsis* root tip cells. *Plant Cell Physiol* 47, 1641-1652.

Ishida H, Yoshimoto K, Izumi M, Reisen D, Yano Y, Makino A, Ohsumi Y, Hanson M R, Mae T. 2008. Mobilization of rubisco and stroma-localized fluorescent proteins of chloroplasts to the vacuole by an ATG gene-dependent autophagic process. *Plant Physiol* 148, 142-155.

Jo E K. 2010. Innate immunity to mycobacteria: vitamin D and autophagy. *Cell Microbiol* 12, 1026-1035.

Karimi M, Inze D, Depicker A. 2002. GATEWAY® vectors for *Agrobacterium*-mediated plant transformation. *Trends Plant Sci* 7, 193-195.

Kirkin V, Lamark T, Johansen T, Dikic I. 2009a. NBR1 cooperates with p62 in selective autophagy of ubiquitinated targets. *Autophagy* 5, 732-733.

Kirkin V, McEwan D G, Novak I, Dikic I. 2009b. A role for ubiquitin in selective autophagy. *Mol Cell* 34, 259-269.

Klionsky D J. 2007. Autophagy: from phenomenology to molecular understanding in less than a decade. *Nat Rev Mol Cell Biol* 8, 931-937.

Klionsky D J, Codogno P, Cuervo A M, Deretic V, Elazar Z, Fueyo-Margareto J, Gewirtz D A, Kroemer G, Levine B, Mizushima N, Rubinsztein D C, Thumm M, Tooze S A. 2010. A comprehensive glossary of autophagy-related molecules and processes. *Autophagy* 6.

Komatsu M, Ichimura Y. 2010. Physiological significance of selective degradation of p62 by autophagy. *FEBS Lett* 584, 1374-1378.

Komatsu M, Kurokawa H, Waguri S, Taguchi K, Kobayashi A, Ichimura Y, Sou Y S, Ueno I, Sakamoto A, Tong K I, Kim M, Nishito Y, Iemura S, Natsume T, Ueno T, Kominami E, Motohashi H, Tanaka K, Yamamoto M. 2010. The selective autophagy substrate p62 activates the stress responsive transcription factor Nrf2 through inactivation of Keap1. *Nat Cell Biol* 12, 213-223.

Komatsu M, Waguri S, Koike M, Sou Y S, Ueno T, Hara T, Mizushima N, Iwata J, Ezaki J, Murata S, Hamazaki J, Nishito Y, Iemura S, Natsume T, Yanagawa T, Uwayama J, Warabi E, Yoshida H, Ishii T, Kobayashi A, Yamamoto M, Yue Z, Uchiyama Y, Kominami E, Tanaka K. 2007. Homeostatic levels of p62 control cytoplasmic inclusion body formation in autophagy-deficient mice. *Cell* 131, 1149-1163.

Larsen K B, Lamark T, Overvatn A, Harneshaug I, Johansen T, Bjorkoy G. 2010. A reporter cell system to monitor autophagy based on p62/SQSTM1. *Autophagy* 6, 784-793.

Legg P D, Collins G B, Litton C C. 1970. Registration of L A Burley 21 tobacco germplasm. *Crop Sci* 10, 212.

Linthorst H J, Brederode F T, van der Does C, Bol J F. 1993. Tobacco proteinase inhibitor I genes are locally, but not systemically induced by stress. *Plant Mol Biol* 21, 985-992.

Liu Y, Schiff M, Czymmek K, Talloczy Z, Levine B, Dinesh-Kumar S P. 2005. Autophagy regulates programmed cell death during the plant innate immune response. *Cell* 121, 567-577.

Mathew R, Karp C M, Beaudoin B, Vuong N, Chen G, Chen H Y, Bray K, Reddy A, Bhanot G, Gelinas C, Dipaola R S, Karantza-Wadsworth V, White E. 2009. Autophagy suppresses tumorigenesis through elimination of p62. *Cell* 137, 1062-1075.

Melendez A, Neufeld T P. 2008. The cell biology of autophagy in metazoans: a developing story. *Development* 135, 2347-2360.

Moreau K, Luo S, Rubinsztein D C. 2010. Cytoprotective roles for autophagy. *Curr Opin Cell Biol* 22, 206-211.

Moriyasu Y, Hattori M, Jauh G Y, Rogers J C. 2003. Alpha tonoplast intrinsic protein is specifically associated with vacuole membrane involved in an autophagic process. *Plant Cell Physiol* 44, 795-802.

Murashige T, Skoog F. 1962. A revised medium for rapid growth and bio assays with tobacco tissue cultures. *Physiol Plant* 15, 473-493.

Nakatogawa H, Suzuki K, Kamada Y, Ohsumi Y. 2009. Dynamics and diversity in autophagy mechanisms: lessons from yeast. *Nat Rev Mol Cell Biol* 10, 458-467.

Pankiv S, Clausen T H, Lamark T, Brech A, Bruun J A, Outzen H, Overvatn A, Bjorkoy G, Johansen T. 2007. P62/SQSTM1 binds directly to Atg8/LC3 to facilitate degradation of ubiquitinated protein aggregates by autophagy. *J Biol Chem* 282, 24131-24145.

Patel S, Dinesh-Kumar S P. 2008. *Arabidopsis* ATG6 is required to limit the pathogen-associated cell death response. *Autophagy* 4, 20-27.

Phillips A R, Suttangkakul A, Vierstra R D. 2008. The ATG12-conjugating enzyme ATG10 Is essential for autophagic vesicle formation in *Arabidopsis thaliana*. *Genetics* 178, 1339-1353.

Reumann S, Voitsekhovskaja O, Lillo C. 2010. From signal transduction to autophagy of plant cell organelles: lessons from yeast and mammals and plant-specific features. *Protoplasma*.

Thompson A R, Doelling J H, Suttangkakul A, Vierstra R D. 2005. Autophagic nutrient recycling in *Arabidopsis* directed by the ATG8 and ATG12 conjugation pathways. *Plant Physiol* 138, 2097-2110.

Thompson A R, Vierstra R D. 2005. Autophagic recycling: lessons from yeast help define the process in plants. *Curr Opin Plant Biol* 8, 165-173.

Wada S, Ishida H, Izumi M, Yoshimoto K, Ohsumi Y, Mae T, Makino A. 2009. Autophagy plays a role in chloroplast degradation during senescence in individually darkened leaves. *Plant Physiol* 149, 885-893.

Walsh C M, Edinger A L. 2010. The complex interplay between autophagy, apoptosis, and necrotic signals promotes T-cell homeostasis. *Immunol Rev* 236, 95-109.

Xiong Y, Contento A L, Nguyen P Q, Bassham D C. 2007. Degradation of oxidized proteins by autophagy during oxidative stress in *Arabidopsis*. *Plant Physiol* 143, 291-299.

Yang Z, Klionsky D J. 2010. Mammalian autophagy: core molecular machinery and signaling regulation. *Curr Opin Cell Biol* 22, 124-131.

Yoshimoto K, Hanaoka H, Sato S, Kato T, Tabata S, Noda T, Ohsumi Y. 2004. Processing of ATG8s, ubiquitin-like proteins, and their deconjugation by ATG4s are essential for plant autophagy. *Plant Cell* 16, 2967-2983.

Yoshimoto K, Jikumaru Y, Kamiya Y, Kusano M, Consonni C, Panstruga R, Ohsumi Y, Shirasu K. 2009. Autophagy negatively regulates cell death by controlling NPR1-dependent salicylic acid signaling during senescence and the innate immune response in *Arabidopsis*. *Plant Cell* 21, 2914-2927.

Yoshimoto K, Takano Y, Sakai Y. 2010. Autophagy in plants and phytopathogens. *FEBS Lett* 584, 1350-1358.

The invention claimed is:

1. A recombinant DNA molecule comprising a polynucleotide operably linked to a heterologous promoter, wherein the polynucleotide sequence is at least 97% identical to the polynucleotide sequence set forth in SEQ ID NO:1, wherein the polynucleotide encodes a protein from the Joka2/p62 family, and wherein the polynucleotide is responsible for conferring increased levels of chlorophylls in response to nutrient deficient conditions in a plant transformed with said recombinant DNA molecule, as compared to an untransformed plant.

2. The recombinant DNA molecule according to claim 1, wherein the polynucleotide is functionally linked with a polynucleotide sequence encoding a marker protein.

3. The recombinant DNA molecule according to claim 2, wherein the marker protein enables in vivo monitoring of production and localization of the protein from the Joka2/p62 family.

4. The recombinant DNA molecule according to claim 2, wherein said marker protein is a yellow fluorescent protein (YFP) or a cyan fluorescent protein (CFP).

5. The recombinant DNA molecule according to claim 1, further comprising an expression cassette with at least one DNA molecule and a selection marker, wherein the selection marker enables a positive selection of plant cells comprising the recombinant DNA molecule incorporated into a plant genome.

6. A method for conferring increased levels of chlorophylls in response to nutrient deficient conditions in a plant, the method comprising:
   transforming a plant with a recombinant DNA molecule comprising a polynucleotide operably linked to a heterologous promoter,
   wherein the polynucleotide is at least 97% identical to the polynucleotide sequence set forth in SEQ ID NO:1,
   wherein the polynucleotide encodes a protein from the Joka2/p62 family,
   and wherein the polynucleotide is responsible for conferring increased levels of chlorophylls in response to nutrient deficient conditions in the transformed plant as compared to an untransformed plant.

7. The recombinant DNA molecule according to claim 2, wherein the marker protein is a fluorescent protein.

* * * * *

SEQUENCE LISTING

```
<160> NUMBER OF SEQ ID NOS: 3

<210> SEQ ID NO 1
<211> LENGTH: 2532
<212> TYPE: DNA
<213> ORGANISM: Nicotiana tabacum

<400> SEQUENCE: 1
atggctatgg agtctgctat tgtgatcaag gtcaagtatg aagagacact caggcgattc      60
aatgctcgtg tcatcaatga gaaacttgat cttaacatgg atggattaag tgacaagatc     120
tttcaacttt tcaacattgc tcgtgatgct gaactcatac taacatatgt tgatgaggat     180
ggcgatgtag ttacacttgt tgatgatgag gatctgcagg acgttatgag gcaggacctg     240
aatcccttgc gaatatctgt gaggttgaat gctgccgaaa gaagtagcag gccttcatct     300
agatctagtg gaagttctac tcccttacga tcacctcggg ttcagcctcc atttccaaac     360
ttgaattcca ctgtttctga tgctctcaag tccgtgccag aacctctgcg tgaaactgta     420
atgaagctct attctgacct gacttcaagg gcctcatcct ctgctccaat ccttgctgag     480
cttgttgatg gtatctctaa gatggggcta tcctactacc agaatcatcc ttcagggtct     540
cagcctgtca agaaacaag cttccctagt ggagcatcta atgaaaatac tatggttgct     600
gatggaggca attcaaatgg taaaagtggg gtgccatcca taaagaagaa cgagccccac     660
acagccctga atgatgcagg gagaacggct aaagctatag aatcagaatt caattatgtg     720
gatgatgcgc tagatgcctg ggtcaagcta agatctaaat caaatgcttt ggaagctgat     780
caaactgaaa ctgcgccatc gtcatccaaa ggtcctaatg ctcacacatt gctggtaaat     840
agtggggagg agaaggataa gaaatttggt gcttgtcctg gtggaaagcc tcttgccttc     900
tcacataata gtgcctcacc tgttccacca gaaaagcctt ctggggagaa gcccagcaag     960
aatcattctg tagctaagcc cgttgatatg ggtggctctg caagtttttgg caaattgaaa    1020 aaatgcatct gggattccg taatgcagat tccagtggca gttctatcaa gatgcctact    1080
ttacgcctag ttccggtccc tgcgaatgaa tgtccatttc cccaggtgcc aaagaacgct    1140
tcacgtctag ttcaggttcc tgcaaatgag tgtccatttt ccggggtgcc aaacgaccct    1200
gtcccacctc ctcttgaggt cccacttaaa aggagtcata atcacagtga tgggactggg    1260
```

```
actattttcc acagaggtgt tcgttgtgat ggttgtggtg ttcatccaat aactggccct    1320
agattcatat ctaaagtaca ggagaactat gatctctgca gcatatgctt tgctgaaatg    1380
ggaaatgatg ctgattacat cagaatggat cgtcctttaa cttaccggca tcccttgtct    1440
ttcaagggtt tacatgatct gcatgctgcg aggtttcgta tcccaactgt tccacatgtc    1500
tctcgaggct atggggtgaa accaggtcgg ccaaagctgg acagccgctt catacaggat    1560
gtcaatatcc tggatggaac catcatggct cccttgactc gatttaccaa gatctggaga    1620
atgaggaata atggtaacct tgtctggcct caaggaactc aacttgtttg gattggggga    1680
gataggttaa gtgataaatt ctctgttgaa ttagagataa ctacagcttg cttggctgtt    1740
gacaaggagc ttgatgtgac agttgatttt actgctcctg tgcatcctgg taggtacata    1800
tcctactgga ggatggcttc gtcttcaggg cagaaatttg gccagcgtgt atgggtgctt    1860
atccaggtcg atgcttcatc aaaccttcca aaaaggagt tggtccacga agcctttcag     1920
gggttaaact tgaatttacc tcctgccggc gatggcgcat ctggatctga cattgtcaat    1980
gtgaatccag aacctcagaa tgtccttcct gagcctaaga gctctagcac aacgatagag    2040
ttggttgatt cagtgactga tgtacaccag aacaaggagc aggaggccat atttcctact    2100
aatgatagct tgttggttgg atttggtgac aagtcaagtt cttctgctcc cggttcatca    2160
atttcatatc caattattga tttgtctgag gaagcaccag cagttacttg tgtggtacca    2220
tccgctgctg tagatacgca ggcaccaccc cagggtgtta gagggaataa cgaaattgag    2280
acgtccctcc tccgtgagct ggaggaaatg gggttcaagc aggtggatct gaacaaggaa    2340
atcttgagga agaatgagta tgacttggag cagtctgttg atgatctctg tggtgttgct    2400
gagtgggatc ctatcctcga agagctggag gaggtgggtt tctccgacaa agaaatgaac    2460
aaggagctgc ttaagaagaa caaggaagc atcaagcgtg ttgtcatgga tcttattgct    2520
ggagagcagt ag                                                        2532

<210> SEQ ID NO 2
<211> LENGTH: 51
<212> TYPE: DNA
<213> ORGANISM: Artificial Sequence
<220> FEATURE:
<223> OTHER INFORMATION: primer 1 example 1

<400> SEQUENCE: 2
ggggacaagt ttgtacaaaa aagcaggctc aatggctatg gagtctgcta t              51

<210> SEQ ID NO 3
<211> LENGTH: 51
<212> TYPE: DNA
<213> ORGANISM: Artificial Sequence
<220> FEATURE:
<223> OTHER INFORMATION: primer 2 example 1

<400> SEQUENCE: 3
ggggaccact ttgtacaaga aagctgggtc ctgctctcca gcaataagat c              51
```